US009782596B2

(12) United States Patent
Vamos et al.

(10) Patent No.: US 9,782,596 B2
(45) Date of Patent: *Oct. 10, 2017

(54) SERVER FOR COMMUNICATION WITH AN IMPLANTABLE MEDICAL DEVICE

(71) Applicant: Boston Scientific Neuromodulation Corporation, Valencia, CA (US)

(72) Inventors: George Vamos, Studio City, CA (US); Kelly H. McClure, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,854

(22) Filed: Nov. 11, 2016

(65) Prior Publication Data

US 2017/0056680 A1    Mar. 2, 2017

Related U.S. Application Data

(63) Continuation of application No. 15/000,226, filed on Jan. 19, 2016, now Pat. No. 9,492,672, which is a
(Continued)

(51) Int. Cl.
*A61N 1/372* (2006.01)
*G06F 19/00* (2011.01)
*H04L 29/08* (2006.01)
*G06F 17/22* (2006.01)
*H04L 29/06* (2006.01)

(52) U.S. Cl.
CPC ..... *A61N 1/37264* (2013.01); *A61N 1/37217* (2013.01); *A61N 1/37282* (2013.01); *G06F 17/2247* (2013.01); *G06F 19/3412* (2013.01); *G06F 19/3418* (2013.01); *H04L 67/02* (2013.01); *H04L 67/12* (2013.01); *H04L 67/42* (2013.01)

(58) Field of Classification Search
None
See application file for complete search history.

(56) References Cited

U.S. PATENT DOCUMENTS 3,942,535 A    3/1976  Schulman
4,208,008 A    6/1980  Smith
(Continued)

FOREIGN PATENT DOCUMENTS

EP    0750921    1/1997
EP    0753327    1/1997
(Continued)

OTHER PUBLICATIONS

Whitehurst, et al. Inventors for AB-195U; U.S. Appl. No. 10/438,374, filed May 15, 2003; entitled "Remote Communications Link for Fully Implantable Miniature Neurostimulation and Sensor System".

*Primary Examiner* — Brian T Gedeon
(74) *Attorney, Agent, or Firm* — Lewis, Reese & Nesmith, PLLC

(57) ABSTRACT

A system and method for modifying the parameters of an implantable medical device includes an implantable medical device that communicates with a remote control device that, in turn, communicates through the browser of a computer or any other device capable of using mark-up language protocol. The computer optionally communicates with other computers and/or devices through a network.

21 Claims, 4 Drawing Sheets

Related U.S. Application Data continuation of application No. 14/696,872, filed on Apr. 27, 2015, now Pat. No. 9,244,898, which is a continuation of application No. 14/201,900, filed on Mar. 9, 2014, now Pat. No. 9,020,603, which is a continuation of application No. 13/766,654, filed on Feb. 13, 2013, now Pat. No. 8,706,254, which is a continuation of application No. 12/783,432, filed on May 19, 2010, now Pat. No. 8,401,661, which is a continuation of application No. 10/857,390, filed on May 28, 2004, now Pat. No. 7,742,821.

(60) Provisional application No. 60/477,604, filed on Jun. 11, 2003.

(56) References Cited

U.S. PATENT DOCUMENTS

| | | | |
|---|---|---|---|
| 4,304,238 A | 12/1981 | Fischer | |
| 4,365,633 A | 12/1982 | Loughman et al. | |
| 4,550,732 A | 11/1985 | Batty et al. | |
| 4,587,970 A | 5/1986 | Holley et al. | |
| 4,926,865 A | 5/1990 | Oman | |
| 5,158,078 A | 10/1992 | Bennett et al. | |
| 5,193,539 A | 3/1993 | Schulman et al. | |
| 5,193,540 A | 3/1993 | Schulman et al. | |
| 5,226,413 A | 7/1993 | Bennett et al. | |
| 5,324,316 A | 6/1994 | Schulman et al. | |
| 5,350,407 A | 9/1994 | McClure et al. | |
| 5,383,915 A | 1/1995 | Adams | |
| 5,456,692 A | 10/1995 | Smith et al. | |
| 5,653,735 A | 8/1997 | Chen et al. | |
| 5,683,432 A | 11/1997 | Goedeke et al. | |
| 5,690,690 A | 11/1997 | Nappholz et al. | |
| 5,752,976 A | 5/1998 | Duffin et al. | |
| 5,752,977 A | 5/1998 | Grevious et al. | |
| 5,792,201 A | 8/1998 | Causey et al. | |
| 5,938,690 A | 8/1999 | Law et al. | |
| 6,003,068 A | 12/1999 | Sopko | |
| 6,083,248 A | 7/2000 | Thompson | |
| 6,249,703 B1 | 6/2001 | Stanton et al. | |
| 6,250,309 B1 | 6/2001 | Krichen et al. | |
| 6,308,102 B1 | 10/2001 | Sieracki et al. | |
| 6,366,572 B1 | 4/2002 | Esterberg et al. | |
| 6,442,432 B2 | 8/2002 | Lee | |
| 6,471,645 B1 | 10/2002 | Warkentin et al. | |
| 6,480,745 B2 | 11/2002 | Nelson et al. | |
| 6,490,487 B1 | 12/2002 | Kraus et al. | |
| 6,497,655 B1 | 12/2002 | Linberg et al. | |
| 6,577,899 B2 | 6/2003 | Lebel et al. | |
| 6,597,951 B2 | 7/2003 | Kramer et al. | |
| 6,604,001 B2 | 8/2003 | Thomas et al. | |
| 6,609,032 B1 | 8/2003 | Woods et al. | |
| 6,622,045 B2 | 9/2003 | Snell et al. | |
| 6,644,322 B2 | 11/2003 | Webb | |
| 6,659,968 B1 | 12/2003 | McClure | |
| 6,665,565 B1 | 12/2003 | Stomberg | |
| 6,804,558 B2 | 10/2004 | Haller et al. | |
| 6,868,309 B1 | 3/2005 | Begelman | |
| 6,878,112 B2 | 4/2005 | Linberg et al. | |
| 6,895,280 B2 | 5/2005 | Meadows et al. | |
| 6,974,437 B2 | 12/2005 | Lebel et al. | |
| 6,978,181 B1 | 12/2005 | Snell | |
| 7,043,305 B2 | 5/2006 | Kenknight et al. | |
| 7,060,030 B2 | 6/2006 | Von Arx et al. | |
| 7,060,031 B2 | 6/2006 | Webb et al. | |
| 7,065,409 B2 | 6/2006 | Mazar | |
| 7,142,923 B2 | 11/2006 | North et al. | |
| 7,146,219 B2 | 12/2006 | Sieracki et al. | |
| 7,155,290 B2 | 12/2006 | Von Arx et al. | |
| 7,181,286 B2 | 2/2007 | Sieracki et al. | |
| 7,203,505 B1 | 4/2007 | Larikka et al. | |
| 7,209,790 B2 | 4/2007 | Thompson et al. | |
| 7,216,000 B2 | 5/2007 | Sieracki et al. | |
| 7,266,412 B2 | 9/2007 | Stypulkowski | |
| 7,324,949 B2 | 1/2008 | Bristol | |
| 7,373,206 B2 | 5/2008 | Sieracki et al. | |
| 7,383,088 B2 | 6/2008 | Spinelli et al. | |
| 7,489,970 B2 | 2/2009 | Lee et al. | |
| 7,505,815 B2 | 3/2009 | Lee et al. | |
| 7,546,340 B2 | 6/2009 | Terasawa | |
| 7,610,099 B2 | 10/2009 | Almendinger et al. | |
| 8,612,554 B2 | 12/2013 | Kikuchi | |
| 2003/0177031 A1 | 9/2003 | Malek | |
| 2004/0088374 A1 | 5/2004 | Webb | |
| 2004/0138518 A1 | 7/2004 | Rise et al. | |

FOREIGN PATENT DOCUMENTS

| | | |
|---|---|---|
| WO | 02/057994 | 7/2002 |
| WO | 03/092769 | 11/2003 |

SERVER FOR COMMUNICATION WITH AN IMPLANTABLE MEDICAL DEVICE

CROSS REFERENCE TO RELATED APPLICATIONS

This is a continuation of U.S. patent application Ser. No. 15/000,226, filed Jan. 19, 2016 (now U.S. Pat. No. 9,492,672), which is a continuation of U.S. patent application Ser. No. 14/696,872, filed Apr. 27, 2015 (now U.S. Pat. No. 9,244,898), which is a continuation of Ser. No. 14/201,900, filed Mar. 9, 2014 (now U.S. Pat. No. 9,020,603), which is a continuation of Ser. No. 13/766,654, filed Feb. 13, 2013 (now U.S. Pat. No. 8,706,254), which is a continuation of Ser. No. 12/783,432, filed May 19, 2010 (now U.S. Pat. No. 8,401,661), which is a continuation of Ser. No. 10/857,390, filed May 28, 2004 (now U.S. Pat. No. 7,742,821), which is a non-provisional of U.S. Provisional Patent Application Ser. No. 60/477,604, filed Jun. 11, 2003. Priority is claimed to these applications, and these applications are incorporated herein by reference in their entireties.

FIELD OF THE INVENTION

The present invention relates to implantable medical devices, and more particularly, to remote control devices for communicating with an implantable medical device and a computer.

BACKGROUND

Current implantable medical devices such as pacemakers, cochlear implants, spinal cord stimulators, and deep brain stimulators, are typically programmed by a specially designed remote control device, or telemetry system, that contains a computer and a radio or magnetic device to communicate with the implantable device. Implantable sensor systems and infusion pumps also require telemetry systems. Implantable sensor systems sense the level of various substances within the body, such as medications, hormones, neurotransmitters, electrolytes, enzymes, gases, and glucose.

The remote control device's computer contains a specific program designed to control the particular type of implant. Some of the remote control devices are complete in themselves. But, some other remote control devices require a larger computer (sometimes called a special-purpose programmer, Clinician's Programmer, or Fitting Station) to configure the remote control parameters, such as speech processing strategies or the adjustability limits of the remote control by the patient.

Clinician's Programmers and their accompanying software programs are very expensive. As the variety of medical devices increases, clinicians are required to stock and track an increasing variety of special purpose devices. A clinician who does not have the appropriate special purpose device cannot offer any assistance to a patient whose treatment requires the device. As a result, patients are restricted to seeking treatment from a limited number of clinics. Patients who must travel long distances to reach one of these qualified clinics are unduly burdened with added expense and inconvenience.

Therefore, a need exists for an implantable medical device remote control system that may be controlled by a clinician without the use of a complex and expensive Clinician's Programmer or Fitting Station.

SUMMARY

The present invention addresses the above and other needs by providing a system for fitting, or altering the parameters of, implantable medical devices using only the patient's own remote control and a general purpose computer equipped with a web browser and network connection, or other communication means, to link to the patient's remote control. Optionally, once a web page from the remote control device is delivered to the browser of the clinician's computer, the clinician can permit a remote user, such as another clinician or the technical support staff of the implant manufacturer, to view and control the parameters displayed on the web page from a remote location. Information in the clinician's browser can be uploaded to a remote site, or server, to be viewed or altered by others.

The present invention eliminates the need for clinicians to be equipped with separate computers and/or software used to manage or control the parameters of the implant. The present invention allows a patient to simply present his remote control device to the clinician, and the clinician is then able to interrogate and intervene as required.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION

Figure 1:
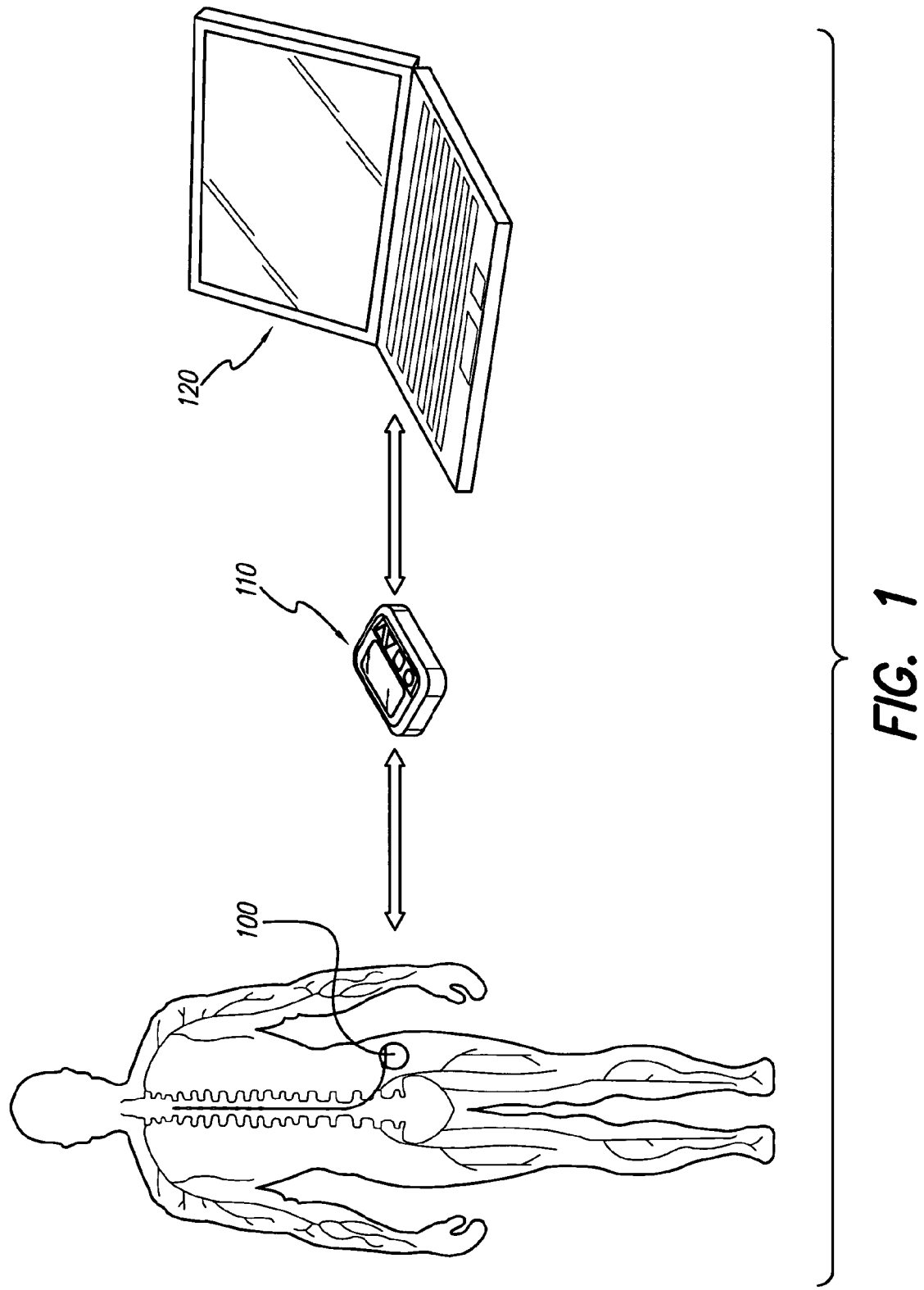
FIG. 1 is a diagram that illustrates a communication system provided by the present invention.

The following description is of the best mode presently contemplated for carrying out the invention. This description is not to be taken in a limiting sense, but is made merely for the purpose of describing the general principles of the invention. The scope of the invention should be determined with reference to the claims.

Recently, others have developed communications systems similar to the present invention in order to monitor and control the behavior of implantable medical devices. For example, U.S. Pat. No. 6,442,432 (issued Aug. 27, 2002) (the '432 patent), incorporated herein by reference, teaches a general purpose computer loaded with a software application that allows the computer to communicate with an interface medical unit connected to the general purpose computer. The interface medical unit also communicates with an implantable medical device (Col. 13, lines 58-63). The '432 patent also teaches an interface medical unit that downloads instructions from a remote expert server and sends the instructions to a remote implantable medical device. Col. 13, lines 10-12. Nevertheless, the '432 patent fails to teach an interface medical unit loaded with server software capable of delivering data to the browser of a general purpose computer.

U.S. Pat. No. 6,497,655 (issued Dec. 24, 2002) (the '655 patent), also incorporated herein by reference, provides a programmer or interface medical unit in communication with an implantable medical device. The programmer or interface medical unit is an interface between the implantable medical device and a remote web-based expert data center (Col. 11, lines 23-27; cols. 15-16, lines 59-18; col. 16, lines 62-64). The remote web-based expert data center has several complex programming software modules that permit a physician to provide clinical care and therapy to a patient (Cols. 21-24, claims 1, 16, and 18). The '655 patent does not indicate that these software modules are delivered to the web-based expert data center from the interface medical unit. Rather, the '655 patent indicates that the complex software modules are already located on the web-based expert data center.

Finally, U.S. patent application Ser. No. 10/438,374 (the '374 application), filed May 15, 2003, also incorporated herein by reference, provides an external device in communication with an implantable medical device. The external device may communicate with distantly located clinician equipment. The '374 application indicates that data is sent from the external device to a server, to another interface device, and finally to a general purpose personal computer (see paragraph 52 and FIG. 3).

Although the three references mentioned above teach systems and methods similar to the present invention, all of these systems and methods lack at least one critical component of the present invention: interface server software on the remote control device itself, which server software delivers data and software modules to a general purpose computer. By loading the remote control device with interface server software, a remote control device manufacturer can permit a clinician to use the remote control device to interface freely with a general purpose computer equipped with commonly available internet browser software. No pre-loaded, complex software modules are needed on the clinician's computer because all of the software modules needed to manipulate and monitor the implantable medical device are already stored on and delivered from the remote control device using interface server software. In essence, the present invention permits a clinician to use communication methods and systems—including the methods and systems of U.S. Pat. Nos. 6,442,432 and 6,497,655 and U.S. patent application Ser. No. 10/438,374—without having to purchase, stock, and operate costly interface equipment.

A simplified representation of the present invention is shown in FIG. 1. The present invention is a system for programming an implantable medical device 100 by means of a hypertext transfer protocol server, or HTTP server, located in a remote control device 110 and a general purpose computer 120. HTTP is a protocol used to request and transmit files between servers and browsers. A server is a software program located on a computer that provides some service on that computer to another computer in a network.

The implantable medical device 100 may be any combination or multiple of an electrical stimulator, an infusion pump, a sensor, or any other implantable medical device whose function can be altered by programmable commands. The remote control device 110 may be implemented in a variety of embodiments, including: a hand held remote control; an amulet; a necklace; a badge; a pin; a wrist-worn device, such as a watch or a bracelet; a talisman; or any other worn or carried device capable of performing the functions of a remote control device 110.

Figure 2:
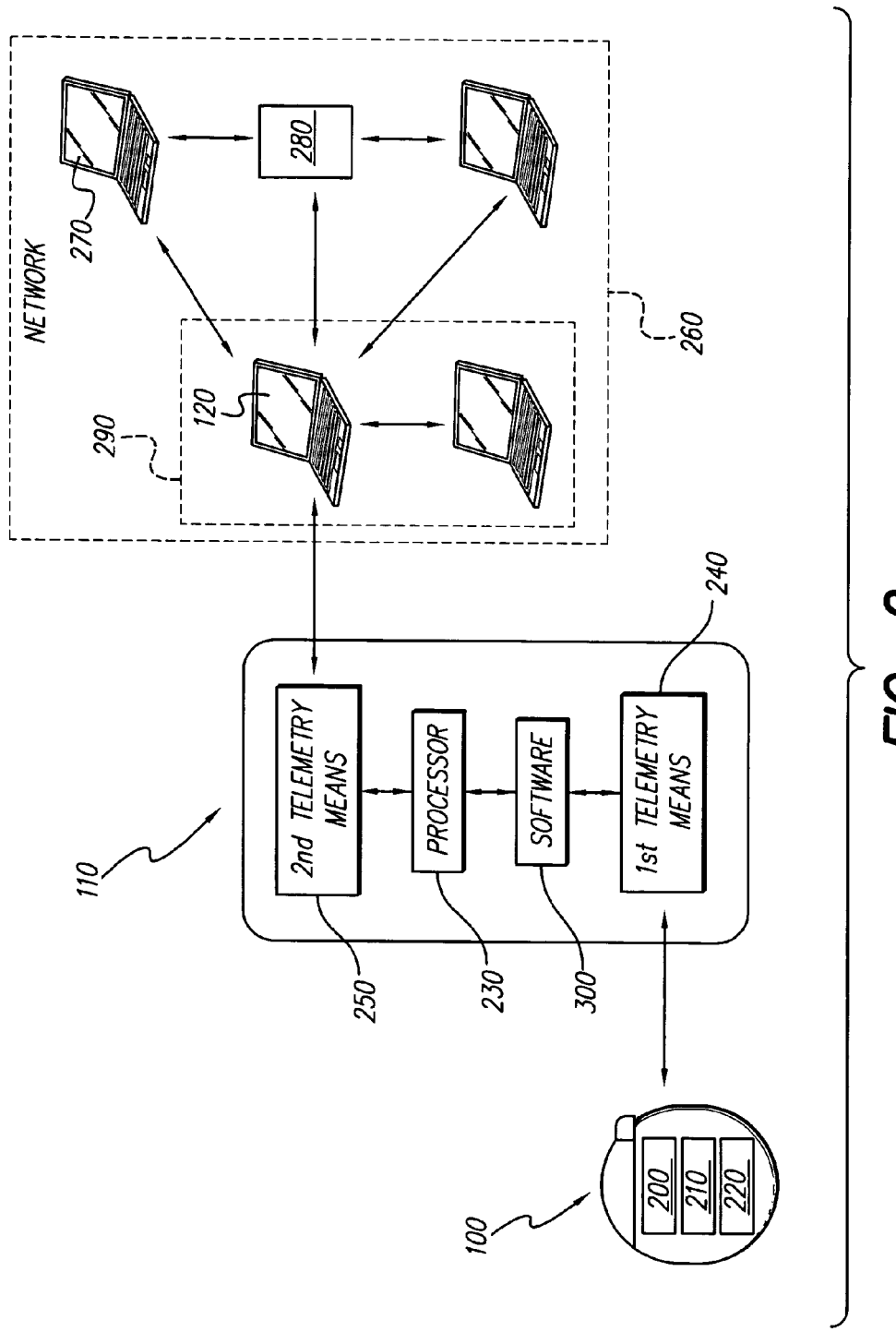
FIG. 2 is a more detailed diagram of the communication system of FIG. 1.

As shown in FIG. 2, implantable medical device 100 contains a processor 200, software 210, and telemetry means 220. Telemetry means 220 may comprise a radio frequency (RF) transmitting circuit, a magnetic coupler, or other means that allows data and commands to be transferred bidirectionally with a device external to the body of a patient. Remote control device 110 also contains a processor 230 including software 300, first telemetry means 240 for communicating with implantable medical device 100, as well as second telemetry means 250, e.g., a wired, RF, magnetic, optical, infra-red, or other telemetry means, for communicating with a network 260. The network 260 may include other computers 120 and 270, one or more servers 280, as well as other devices. Encryption and/or decryption of information may be employed by the remote control device 110, the one or more servers 280, the computer 120, and/or any other data communications device of the present invention.

Figure 3:
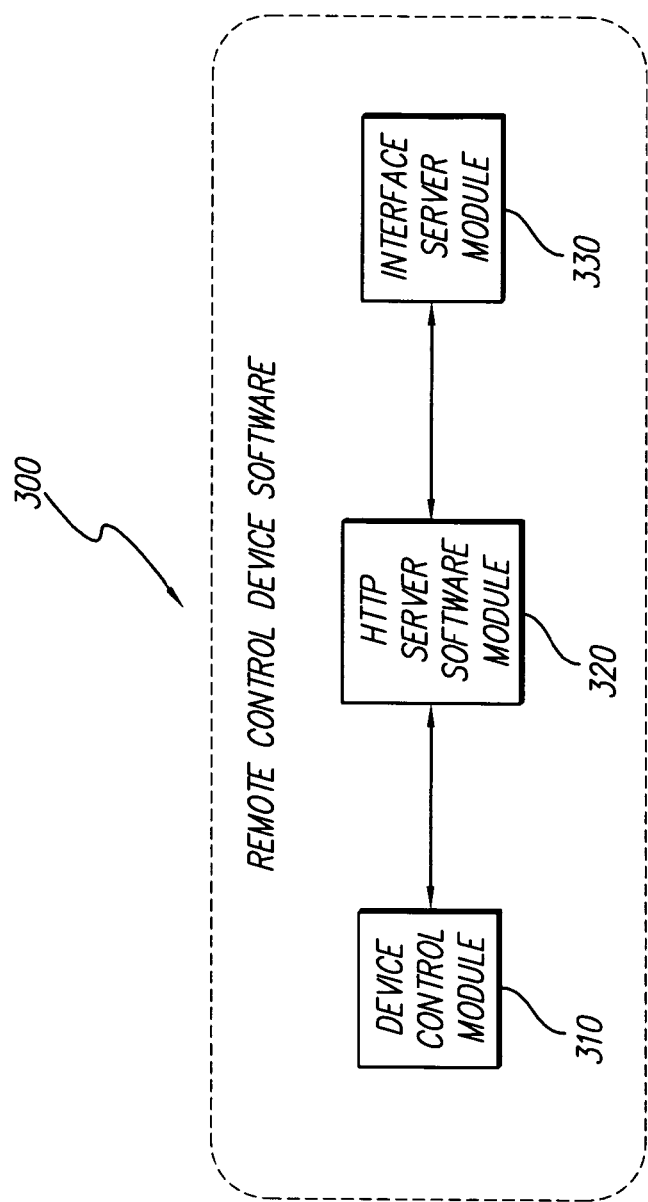
FIG. 3 is a diagram of computer software components of a remote control device used with the present invention.

As shown in FIG. 3, remote control device software 300 contains the following software modules: a device control module 310, an HTTP server software module 320, and an interface server module 330. Not shown in FIG. 3 but present within the remote control device 300 are necessary hardware components that respond to and carry out the instructions and program controls mandated by the various software modules. Such hardware components will be readily understood by one of ordinary skill in the art to be a part of the present invention. Device control module 310 is the basic control program used to communicate with the implantable medical device 100. Device control module 310 controls the operation of implantable medical device 100 (FIG. 2) based on a set of behavior or control variables, such as electrical stimulation pulse amplitude and frequency.

HTTP server software module 320 permits "server side scripts", also called Common Gateway Interference, or CGI, scripts, to communicate to any "client" program within the reach of network 260 (FIG. 2) (wired or wireless) that supports the HTTP protocol. HTTP server software module 320 acts as a way of connecting the "server" with the "client". Alternately, the server side scripts can act as network clients to other network devices such as printers, earphones, global positioning systems, microphones, telephones, cell phones, and modems.

Interface server module 330 manages device control module 310 variables. Interface server module 330 is identified to HTTP server software module 320 by a special symbolic address, called a Universal Resource Locator, or URL. Interface server module 330 assembles messages containing codes for hypertext markup language, or HTML, forms which are passed to a "client" browser and can be presented as documents with optional fields that can be filled with data. A "client" browser is a program that permits a computer terminal to display files and other data sent from a server.

Referring again to FIG. 2, the "client" browser is filled with files or other data from the remote control device 110 and displayed in the terminal of computer 120. Computer 120 is capable of communicating with remote control device 110 and with other computers and devices capable of communicating using HTTP protocol. Remote control device 110 is capable of communicating with computer 120 and other computers and devices capable of communicating using HTTP protocol. Computer 120 and remote control device 110 communicate using wired or wireless means, including infrared, acoustic, ultrasound, magnetic, fiberoptic, USB, Firewire, ilink, or other communication channels known by those of ordinary skill in the art.

Computer 120 must be equipped with a display program compatible with the HTTP protocol, such as a web browser program. Information in the display program can be transferred to and from other computers 270, servers 280, and other devices capable of reading and writing information in a local or general network by means of a wired, wireless, optical, satellite, or other communication channel known by those of ordinary skill in the art. For example, display applets or other configuration management information from another device located on the general network 260 may be sent to the web browser program of computer 120. Such applets may increase the aesthetics and functionality of the program displayed in the web browser. At a minimum, however, the computer 120 must be equipped with a display program compatible with the HTTP protocol. Then, all other code compatible with the HTTP protocol may be transmitted from a network to the computer 120 to increase the functionality of the computer 120. A limited amount of such code may in turn be transmitted to the remote control device 110.

Figure 4:
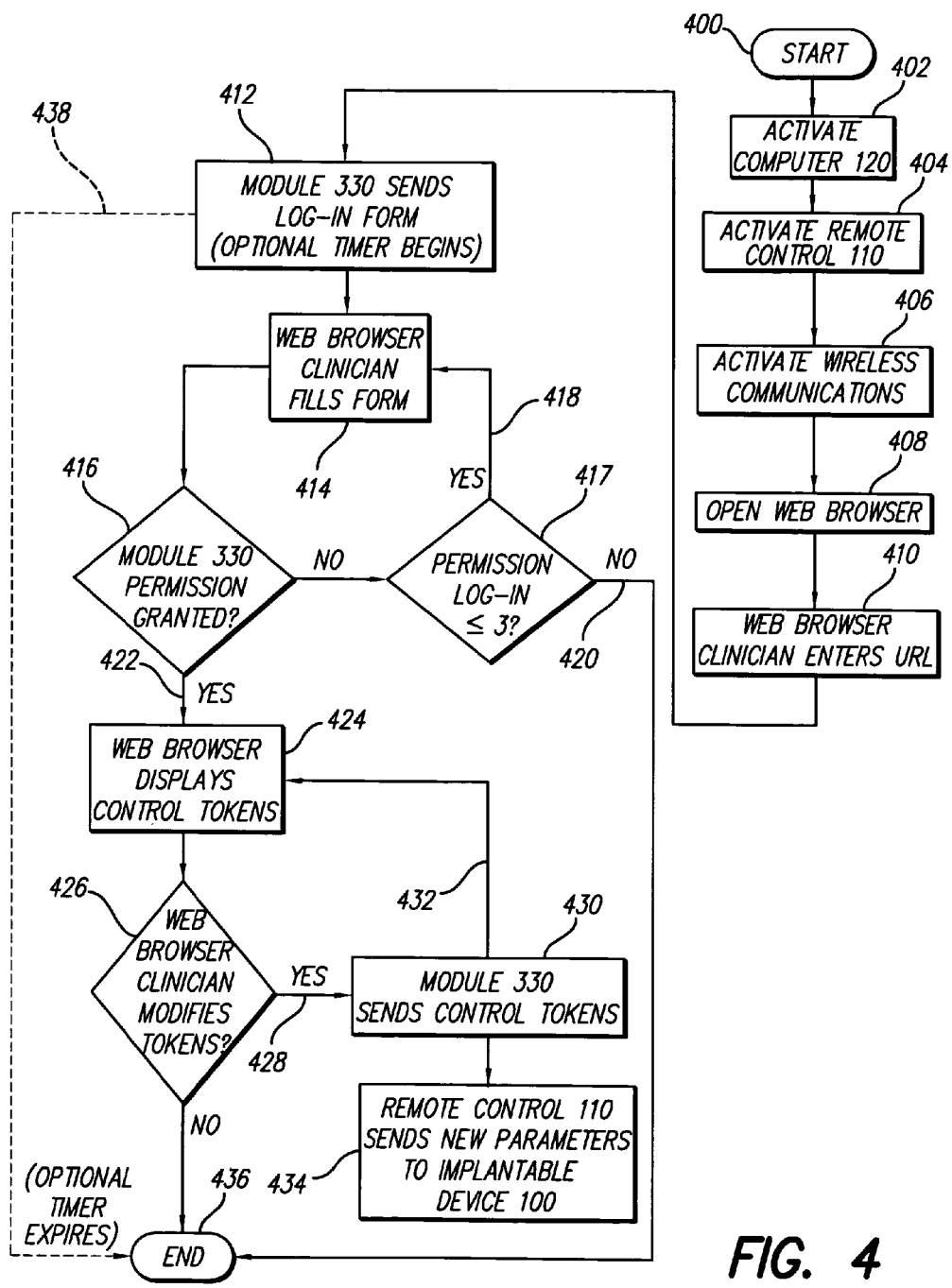
FIG. 4 is a flow chart illustrating steps for using a system of the present invention.

Referring to FIG. 4, following are sequential steps of an embodiment of a method of operating the system of the present invention. A clinician begins at step 400 by placing the remote control device 110 within communicating range of the implantable medical device 100 and the computer 120. The clinician then continues by executing, in any preferred order, the following four steps: step 402 of activating computer 120, step 404 of activating remote control 110, step 406 of activating the wireless communications between implanted device 100 and remote control 110, and step 408 of opening a web browser within computer 120. The clinician then enters the URL for the "server side script" software of the remote control device 110 into the browser at step 410. The interface server module 330 sends a "login form" at step 412 to the browser opened in the computer 120, featuring fields for identification, password, or other security tokens. The clinician fills in the form and submits it to the interface server module 330 at step 414.

The interface server module 330 examines the filled-in form and decides if permission for display or modification of implanted device control parameters should be granted at step 416. If the permission is denied, the denial is counted at step 417. If permission has been denied, e.g., three times or less, then interface server module 330 sends an error message with a new "login form" to the browser at step 418. If permission is denied, e.g., more than three times, the interface server module sends a termination message to the browser at step 420 indicating that login attempts were unsuccessful, and the session is terminated. If the permission is granted, the interface server module 330 sends a form to the computer 120 at step 422 that is displayed in the browser with control tokens at step 424 for modifying the parameters of the remote control device 110.

At this point the clinician may modify each control variable through the browser at step 426. As the clinician modifies each control variable through the browser at step 428, a request is sent to the interface server module 330 within the remote control 110 at step 430. The interface server module 330 responds to each request from the clinician by sending out a new page displaying the control tokens for future action in the browser and the current device status at step 432. The interface server module also responds to each request from the clinician by sending the new parameters to the implantable device 100 at step 434. Alternatively, a request may be sent to the interface server module 330 to deliver all new parameters in a group to the implantable device 100 after all control variables have been modified by the clinician.

Alternately, when the clinician selects a control token for terminating the interaction at step 426, the interface server module 330 stops sending forms to computer 120 and the session terminates at step 436. Optionally, the login process may start a timer (preferably located within the remote control device 110) which specifies a maximum time for the interaction, after which the interface server module 330 stops sending out pages at optional step 438.

Once a session has begun, it is possible that errors may occur during a session that could potentially jeopardize the health of the patient. In order to avoid endangering the patient, interface server module 330 requests device control module 310 to switch the implantable medical device 100 to safe operations. Safe operations are a predefined set of parameters upon which the implantable medical device 100 can properly function without endangering the patient. By entering into safe operations, the system of the present invention limits or stops the therapy session whenever there is an error in order to ensure the safety of the patient. Safe operations continue until the clinician initiates a new session or until the error is resolved.

Additionally, information coming from computer 120 and remote control device 110 may be retrieved from arbitrary server systems on a local 290 or general network 260. Local network 290 is located entirely within a single building and is any network of any devices capable of communicating with each other and with computer 120. These portions may include pages using markup language (such as html, xml, xhtml, sgml, dhtml, and any derivative thereof), graphics, or client side logic (sometimes called scripts or applets). Markup language is a coding system used to structure, index, and link files for presentation in a browser. As a first option, remote control device 110 or the browser (under the control of an applet or script) may upload patient or device data to a server on the network. As a second option, the web page and applets may exchange data with a server 280 and/or database at a remote site on general network 260. General network 260 may include local network 290 and may also include any data transfer network of devices, such as an intranet or internet established through wired (e.g., telephone lines) and/or wireless (e.g., cell phone towers or satellite transmissions) means. Information supplied from a remote server 280 to computer 120 across the general network 260 could provide a common client desktop interface, where a clinician could see the history of the patient with other clinicians.

Network communication permits both easy file sharing and file upgrading. Information transferred over a network from a remote location is more easily upgraded than cumbersome and expensive software packages running in a clinician's office. In addition, remote server 280 or the remote database can be used to backup and clone remote control device 110 as needed.

It is thus seen that remote control device 110 provides a gateway between a physician's computer and a patient's implantable device. Remote control device 110 may further include a security device to prevent unauthorized users from impermissibly altering the parameters of a patient's implantable medical device. For example, the security device may prevent impermissible alteration by acting as a physical enabler for communication to remote control 110 that only one with possession of remote control device 110 may activate. One embodiment of such a physical enabler is a recessed switch that, when activated, enables communications with remote control device 110 for a limited time, such as 15 minutes. After the time expires, the switch is automatically deactivated and must again be activated in order for communications to continue. Other embodiments of physical enablers may include key combinations, keys and locks, and other physical security tokens.

Advantageously, both patients and clinicians, spread out over a large area, may enjoy the benefits of the present invention. The present invention permits implant patients the freedom to seek care from any able clinician equipped with a general purpose computer. Clinicians are no longer required to pay for and maintain expensive special-purpose programmers and similar complex stations to support the programming and fitting of implantable medical devices. Further, clinicians may also enjoy un-cluttering their fitting areas by reducing the number of programming systems in each area.

While the invention herein disclosed has been described by means of specific embodiments and applications thereof, numerous modifications and variations could be made thereto by those skilled in the art without departing from the scope of the invention set forth in the claims.

What is claimed is:

1. A system, comprising:
   an implantable medical device; and
   a first device configured to directly wirelessly communicate with the implantable medical device, wherein the first device comprises a server configured to communicate with a second device, and wherein the server is configured to receive a request from the second device and transmit information to the second device in response to the request.

2. The system of claim 1, wherein the first device is configured to wirelessly communicate with the second device.

3. The system of claim 1, wherein the first device is configured to communicate with the second device by a wired connection.

4. The system of claim 1, wherein the information is one or more of status information pertaining to the implantable medical device, a security token, a device control token, and a communication termination control token.

5. The system of claim 1, wherein the information comprises information interpretable by a web browser program of the second device.

6. The system of claim 1, wherein the information comprises a login form.

7. The system of claim 1, wherein the first device is further configured to receive from the second device operational parameters for the implantable medical device after receipt of the request, and wherein the first device is configured to communicate the operational parameters to the implantable medical device.

8. The system of claim 1, wherein the request comprises operational parameters for the implantable medical device, and wherein the first device is configured to communicate the operational parameters to the implantable medical device.

9. The system of claim 1, wherein the first device is hand-holdable and portable.

10. The system of claim 1, wherein the first device is configured to be worn by a user.

11. The system of claim 1, wherein the first device comprises a remote control for the implantable medical device.

12. A communication device, comprising:
    telemetry circuitry configured to communicate with an implantable medical device and with an external device;
    a server configured to receive via the telemetry circuit a request from a browser of the external device and to transmit via the telemetry circuitry information to the browser in response; and
    a portable, hand-holdable housing containing the telemetry circuitry and the server.

13. The device of claim 12, wherein the information is one or more of status information pertaining to the implantable medical device, a security token, a device control token, and a communication termination control token.

14. The device of claim 12, wherein the information comprises a login form.

15. The device of claim 12, wherein the telemetry circuitry is configured to wirelessly communicate directly with the implantable medical device and wirelessly communicate directly with the external device.

16. The device of claim 12, wherein the telemetry circuitry is configured to communicate directly with the external device by a wired connection.

17. The device of claim 12, wherein the telemetry circuitry comprises first telemetry circuitry configured to communicate with the implantable medical device, and second telemetry circuitry configured to communicate with the second device.

18. The device of claim 12, wherein the server is further configured to receive from the external device operational parameters for the implantable medical device after receipt of the request, and wherein the telemetry circuitry is configured to wirelessly communicate the operational parameters to the implantable medical device.

19. The device of claim 12, wherein the request comprises operational parameters for the implantable medical device, and wherein the telemetry circuitry is configured to wirelessly communicate the operational parameters to the implantable medical device.

20. The device of claim 12, wherein the device is configured to be worn by a user.

21. The device of claim 12, wherein the device is configured to operate as a remote control from the implantable medical device.

* * * * *